(12) United States Patent
Sato

(10) Patent No.: US 7,344,250 B2
(45) Date of Patent: Mar. 18, 2008

(54) COLOR PRESENTING METHOD, COLOR SAMPLE BOOK, AND COLOR PRESENTING APPARATUS

(75) Inventor: Takayuki Sato, Tokyo (JP)

(73) Assignee: Toyo Ink Mfg. Co., Ltd., Tokyo (JP)

( * ) Notice: Subject to any disclaimer, the term of this patent is extended or adjusted under 35 U.S.C. 154(b) by 365 days.

(21) Appl. No.: 11/071,189

(22) Filed: Mar. 4, 2005

(65) Prior Publication Data

US 2005/0195363 A1 Sep. 8, 2005

(30) Foreign Application Priority Data

Mar. 5, 2004 (JP) ............................ P2004-061875

(51) Int. Cl.
*A61B 3/00* (2006.01)
*A61B 3/02* (2006.01)
(52) U.S. Cl. ...................... 351/242; 351/200
(58) Field of Classification Search ................ 359/242; 351/242
See application file for complete search history.

(56) References Cited

U.S. PATENT DOCUMENTS

| | | | | |
|---|---|---|---|---|
| 5,619,194 A | * | 4/1997 | Belfer | 340/907 |
| 2004/0085327 A1 | * | 5/2004 | Jones et al. | 345/591 |
| 2004/0212815 A1 | * | 10/2004 | Heeman et al. | 358/1.9 |
| 2006/0139644 A1 | * | 6/2006 | Kahn et al. | 356/406 |

FOREIGN PATENT DOCUMENTS

| | | |
|---|---|---|
| JP | 8-331402 | 12/1996 |
| JP | 2002-169473 | 6/2002 |
| JP | 2003-5654 | 1/2003 |

* cited by examiner

*Primary Examiner*—Jordan Schwartz
*Assistant Examiner*—James C Jones
(74) *Attorney, Agent, or Firm*—Oblon, Spivak, McClelland, Maier & Neustadt, P.C.

(57) ABSTRACT

A set of each of a plurality of colors is provided which can be distinguished from each other by a color-blind person and a plurality of colors which can be distinguished from each other by a person of normal color vision but are recognized as the each color by the color-blind person.

2 Claims, 5 Drawing Sheets

COLOR PRESENTING METHOD, COLOR SAMPLE BOOK, AND COLOR PRESENTING APPARATUS

CROSS REFERENCE TO RELATED APPLICATION

This application claims benefit of priority under 35 U.S.C. § 119 to Japanese Patent Application No.2004-061875, filed on Mar. 5, 2004, the entire contents of which are incorporated by reference herein.

BACKGROUND OF THE INVENTION

1. Field of the Invention

The present invention relates to a color presenting method, a color sample book, and a color presenting apparatus and, more particularly, to a color presenting method, a color sample book, and a color presenting apparatus with consideration given to color-blind persons.

2. Description of the Related Art

Hitherto, in the fields where color plays an important role in designing such as the printing field typified by offset and gravure, the architecture field using wall paper, tiles, and the like, and the sign display field using paints and marking films for a sign, a color chart typified by a color sample book is used as communication means at the time of ordering a material or requesting for manufacture. The color chart is effective as a tool used by an orderer/client to accurately make his/her intended color known to an order receiver/accepter and is also widely used as indices of usable colors when an orderer/client selects color in designing (refer to Japanese Patent Application Laid-Open Nos.8-331402, 2002-169473, and 2003-5654).

Meanwhile, color deficiency or dyschromatopsia occurs one in 20 Japanese men and one in 500 Japanese women. It is written in many reports that many of color deficiencies are caused by some mutation in any of three visual pigment genes of red, green, and blue. Although people having color deficiency or dyschromatopsia can differentiate colors in a considerably wide range, they confuse some colors. They often erroneously recognize color information provided by the color chart.

To address this problem, in recent years, designs such as barrier-free design and universal design are in demand. In designing, colors distinguished by a person of normal color vision can be easily selected by using the color chart but it is very difficult to select colors which can be distinguished by a color-blind person. Consequently, under present circumstances, colors are selected so that a color-blind person can also distinguish colors on the basis of experiments and psychologically proved results by trial and error.

SUMMARY OF THE INVENTION

The present invention has been achieved in consideration of the above points and its object is to provide a color presenting method, a color sample book, and a color presenting apparatus for color-blind persons.

Another object of the invention is to provide a color presenting method, a color sample book, and a color presenting apparatus which enables a person of normal color vision to easily design colors with consideration given to color-blind persons.

To achieve the object, there is provided a color presenting method for presenting a plurality of colors which can be distinguished from each other by a color-blind person.

According to the invention, color presentation for color-blind persons can be performed.

In a preferred embodiment of the invention, for each of colors which can be distinguished also by a color-blind person, a set of colors that can be distinguished by a person of normal color vision but are recognized as the each color by the color-blind person is presented.

In the embodiment, a person of normal color vision can easily design colors in consideration of color-blind persons without performing trial and error.

To achieve the object, there is also provided a color sample book, wherein a plurality of colors which can be distinguished from each other by a color-blind person are painted.

According to the invention, a color sample book for a color-blind person can be provided.

In a preferred embodiment of the invention, for each of colors which can be distinguished from each other also by a color-blind person, a set of colors that can be distinguished from each other by a person of normal color vision but are recognized as the each color by the color-blind person is painted.

By using the color sample book, a person of normal color vision can easily design colors in consideration of color-blind persons without performing trial and error.

To achieve the object, there is also provided a color presenting apparatus comprising: a storage for storing information of a plurality of colors which can be distinguished from each other by a color-blind person; a color display; and a controller for displaying a plurality of colors which can be distinguished from each other by the color-blind person on the color display on the basis of information of the plurality of colors which can be distinguished from each other by the color-blind person, stored in the storage.

According to the invention, a color presenting apparatus for color-blind persons can be provided.

In a preferred embodiment of the invention, the storage stores, for information of each of colors which can be distinguished by the color-blind person, a set of information of a plurality of colors which can be distinguished from each other by a person of normal color vision but are recognized as the each color by the color-blind person, and the controller displays each of the colors which can be distinguished by the color-blind person and a plurality of colors which can be distinguished from each other by a person of normal color vision but are recognized as the each color by the color-blind person so as to be associated with each other on the color display on the basis of the information stored in the storage.

By using the color presenting apparatus, a person of normal color vision can easily design colors in consideration of color-blind persons without performing trial and error.

The nature, principle and utility of the invention will become more apparent from the following detailed description when read in conjunction with the accompanying drawings.

DESCRIPTION OF THE PREFERRED EMBODIMENTS

Embodiments of a color presenting method, a color sample book, and a color presenting apparatus of the invention will be described in detail hereinbelow with reference to the drawings.

First, dyschromatopsia referred to as a precondition in the invention will be described. Dyschromatopsia in the invention is roughly divided into some kinds such as monochromatism where only one kind of cone photopigments of eyes functions, dichromatism where two kinds of cones function, and anomalous trichromatism where although three kinds of cones function, a shift occurs in the wavelength characteristic of one of them. The dichromatism and anomalous trichromatism are sub-divided into protanomalous, deuteranomalous, and tritanomalous in accordance with a cone in which a change or dysfunction occurs. In the protanomalous and deuteranomalous, the ways colors are seen are relatively close to each other. Consequently, protanomalous and deuteranomalous are generically called "red-green blindness" which occurs in 5% of Japanese men. Tritanomalous is rare. ("Mechanism of Color Sense and Dyschromatopsia" by Mitsuo Ikeda and Yoshio Nakajima, Ophthalmology Mook No. 16, 1982).

The basic idea of the invention is to select a plurality of colors which can be significantly distinguished by a color-blind person from a color space recognized by a color-blind person and present the selected colors. In this manner, a color chart for color-blind persons can be basically provided. Further, a plurality of colors in a color space recognized by a person of normal color vision are associated with basic colors in the color chart for color-blind persons. By using the color configuration presented, a color-blind person can select a plurality of colors which can be distinguished from each other by himself/herself, and a person of normal color vision can select a plurality of colors which can be distinguished from each other by himself/herself and also by a color-blind person.

Figure 1:
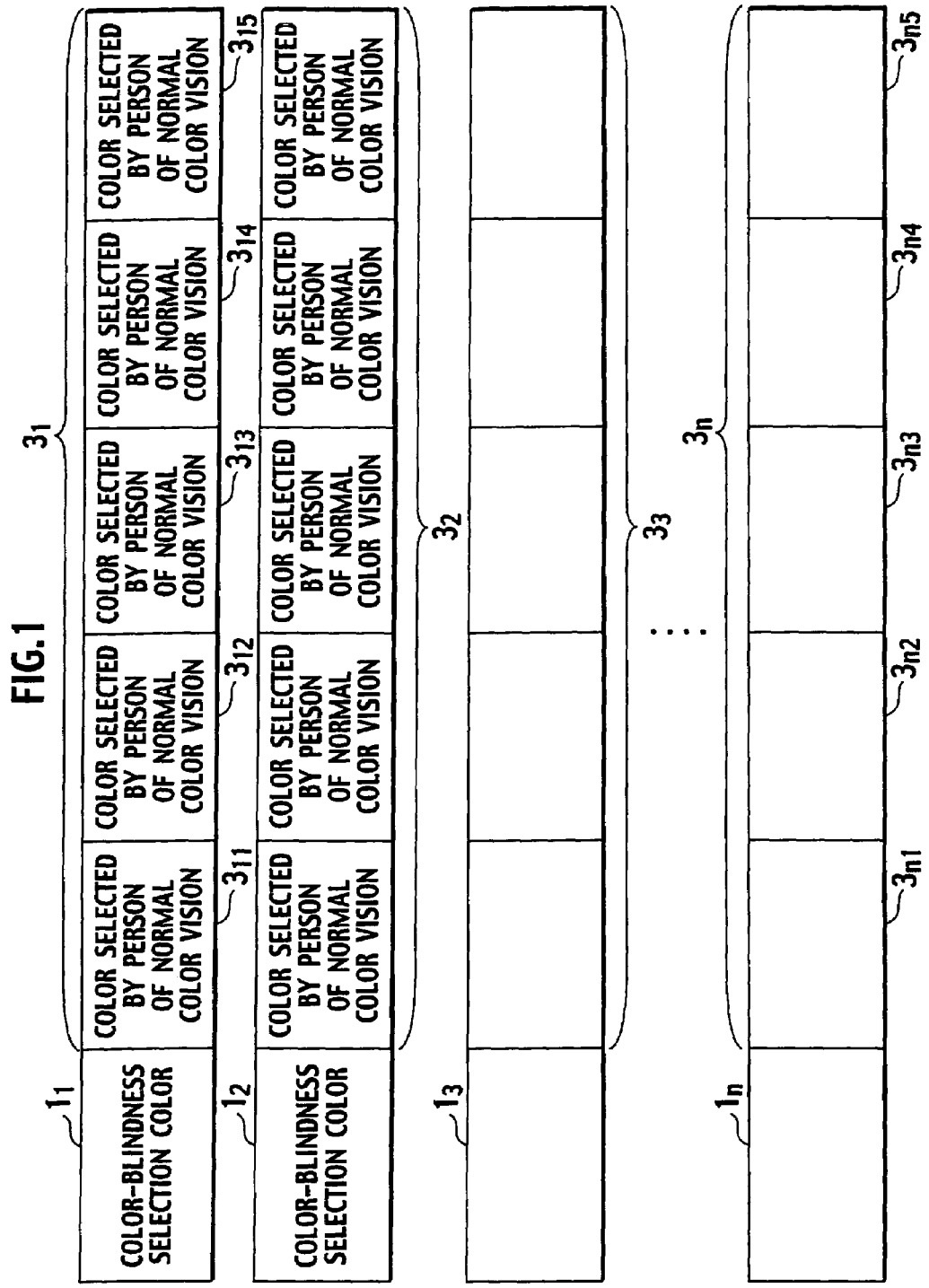
FIG. 1 is a diagram showing an embodiment of a color presenting method of the invention.
Figure 2:
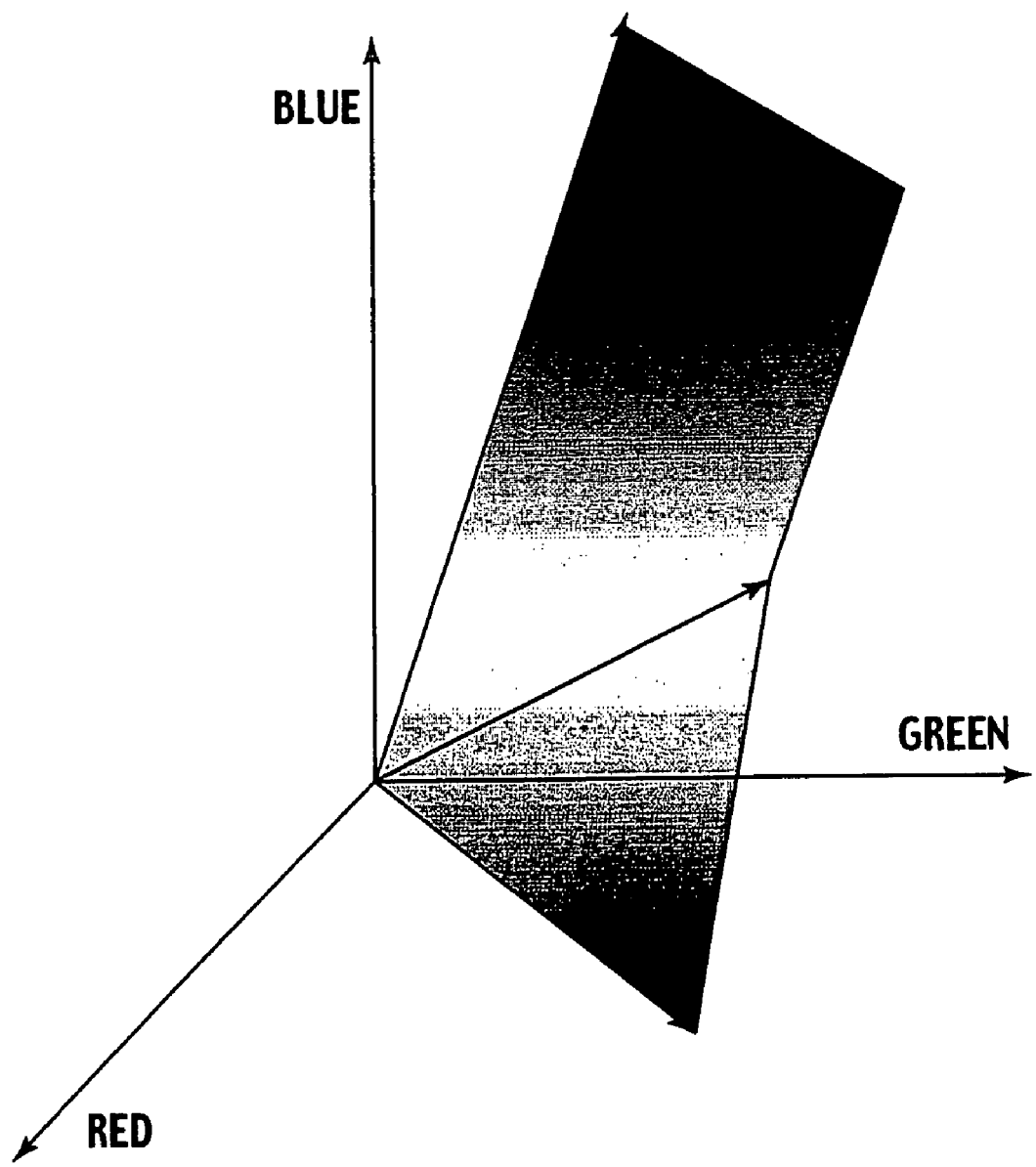
FIG. 2 is a conceptual diagram showing a color space which can be recognized in red-green blindness.

FIG. 1 is a diagram illustrating an embodiment of a color presenting method of the invention. FIG. 2 is a conceptual diagram of a color space which can be recognized in red-green blindness.

As shown in FIG. 2, a color-blind person having red-green blindness has only a two-dimensional color space in a three-dimensional color space of a person of normal color vision. Specifically, all of colors in the three-dimensional color space distinguished by a person of normal color vision are projected to the two-dimensional plane for the color-blind person. Therefore, it can happen that two colors which can be distinguished from each other by a person of normal color vision are seen as the same color and cannot be distinguished from each other by a color-blind person.

Consequently, in the embodiment of the color presenting method of the invention, as shown in FIG. 1, a plurality of colors which can be significantly distinguished from each other by a color-blind person are selected from a color space recognized by a color-blind person and presented as indices used when a color-blind person selects a color. Hereinbelow, the plurality of colors presented will be called color-blindness selection colors $1$ ($1_1$ to $1_n$). Although the number of the color-blindness selection colors $1$ varies according to applications, usually, it ranges from about 2 to 1000.

In the embodiment, the plurality of colors in the color space recognized by a person of normal color vision are associated with the color-blindness selection colors ($1_1$ to $1_n$) Hereinbelow, the associated colors will be called colors $3$ to be selected by person of normal color vision. Plainly, "a plurality of colors selected by a person of normal color vision" associated with a certain color-blindness selection color are colors which can be distinguished from each other by a person of normal color vision but are seen as the same color-blindness selection color by a color-blind person. For example, colors $3_1$ selected by person of normal color vision are associated with the color-blindness selection color $1_1$. In the embodiment, five colors selected by person of normal color vision (for example, colors $3_{11}$ to $3_{15}$ selected by person of normal color vision) are associated with one color-blind person selection color (for example, the color-blindness selection color $1_1$). From the viewpoint of the color space, when a person of normal color vision sees, a color-blindness selection color is typically one of the corresponding plurality of colors selected by a person of normal color vision but does not always exist in the colors selected by person of normal color.

By preparing such a combination of colors and presenting it to a color-blind person, the color-blind person can select a desired color from a plurality of color-blindness selection colors. Therefore, by extracting a plurality of proper colors as the plurality of color-blindness selection colors from the color space recognized by a color-blind person, a color-blind person can select a desired color from the color-blindness selection colors.

A scene that a person of normal color vision selects a color is now assumed. Also in the case where a person of normal color vision selects a desired color, the combination of colors is presented. Although the person of normal color vision can select a desired color from the color-blindness selection colors like a color-blind person, if a satisfactory color cannot be obtained from only the color-blindness selection colors, a color can be selected from a selection range including colors to be selected by person of normal color vision. In such a manner, an opportunity of designing in a more natural combination of colors can be provided to a person of normal color vision. In this case, it is preferable to make a condition that two or more colors are not selected from each group of colors selected by a person of normal color vision corresponding to each color-blindness selection color. Two colors selected from the same group of colors selected by person of normal color vision, in other words, two colors selected by person of normal color vision corresponding to the same color-blindness selection color are colors which can be distinguished by a person of normal color vision but cannot be distinguished from each other by a color-blind person. That is, under the constraint that a person of normal color vision does not select two or more colors from a group of colors selected by person of normal color vision corresponding to the same color-blindness selection color, for example, in arrangement of the selected colors, designing of colors considering color-blind persons can be realized.

Although five colors selected by person of normal color vision are assigned to one color-blindness selection color in the above description, the invention is not limited to this number. A number of continuous colors selected by a person of normal color vision correspond to one color-blindness selection color in the color space shown in FIG. 2 and a proper number of colors selected by person of normal color vision which are distinguished from each other may be selected. Moreover, the number of corresponding colors selected by person of normal color vision may vary according to a color-blindness selection color.

It is preferable to present a color name and a color value (CMYK values and RGB values) for each of the color-blindness selection colors and colors selected by person of normal color vision.

FIG. 1 shows the concept of the color presenting method of the invention. Concretely, there are various presenting means as follows.

Figure 3:
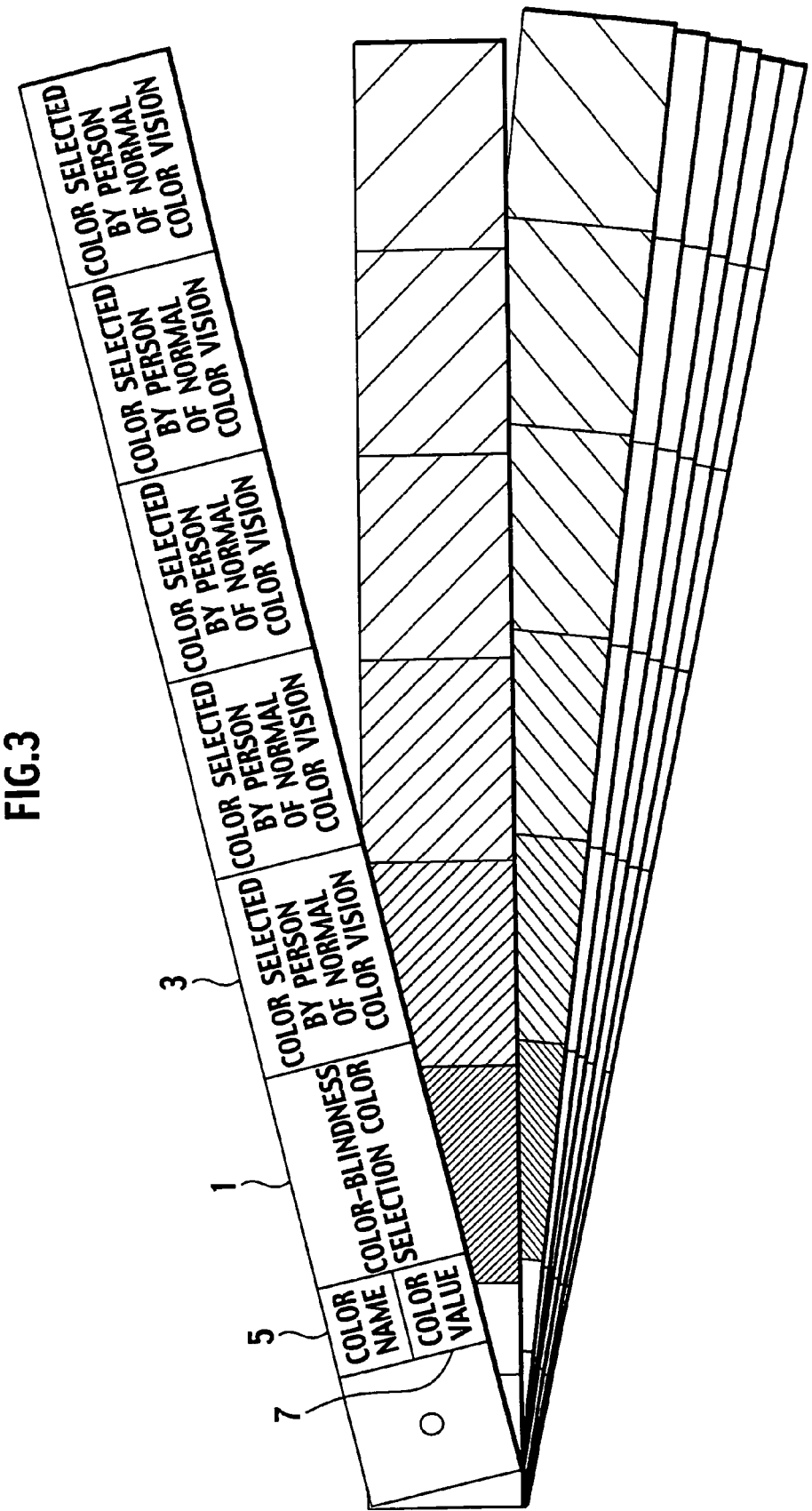
FIG. 3 is a diagram showing an embodiment of the case where the color presenting method of the invention is applied to a color sample book.

FIG. 3 is a diagram showing an embodiment in the case of applying the color presenting method of the invention to a color sample book. FIG. 3 shows one sheet of color samples for each color-blindness selection color. In the color-blindness selection colors $1_1$ to $1_n$ and the colors $3_{11}$ to $3_{n5}$ selected by person of normal color vision, the corresponding colors are actually painted. For each of the color-blindness selection colors $1_1$ to $1_n$, the color name 5 and the color value 7 are also indicated. As described above, the color name and the color value may be also indicated to each color selected by person of normal color vision.

By the color sample book, the color presenting method described by referring to FIG. 1 can be concretely realized.

A color sample book in which a plurality of selected colors are shown in one sheet may be also used. Alternately, the form of a so-called color chart in which all of colors are arranged in a single sheet may be also employed. With respect to arrangement of colors on the color chart, the arrangement shown in the conceptual diagram of FIG. 1 is preferable in practice because the columns are aligned. The various forms are achieved as a result of consideration of easiness of use and the like as before.

Figure 4:
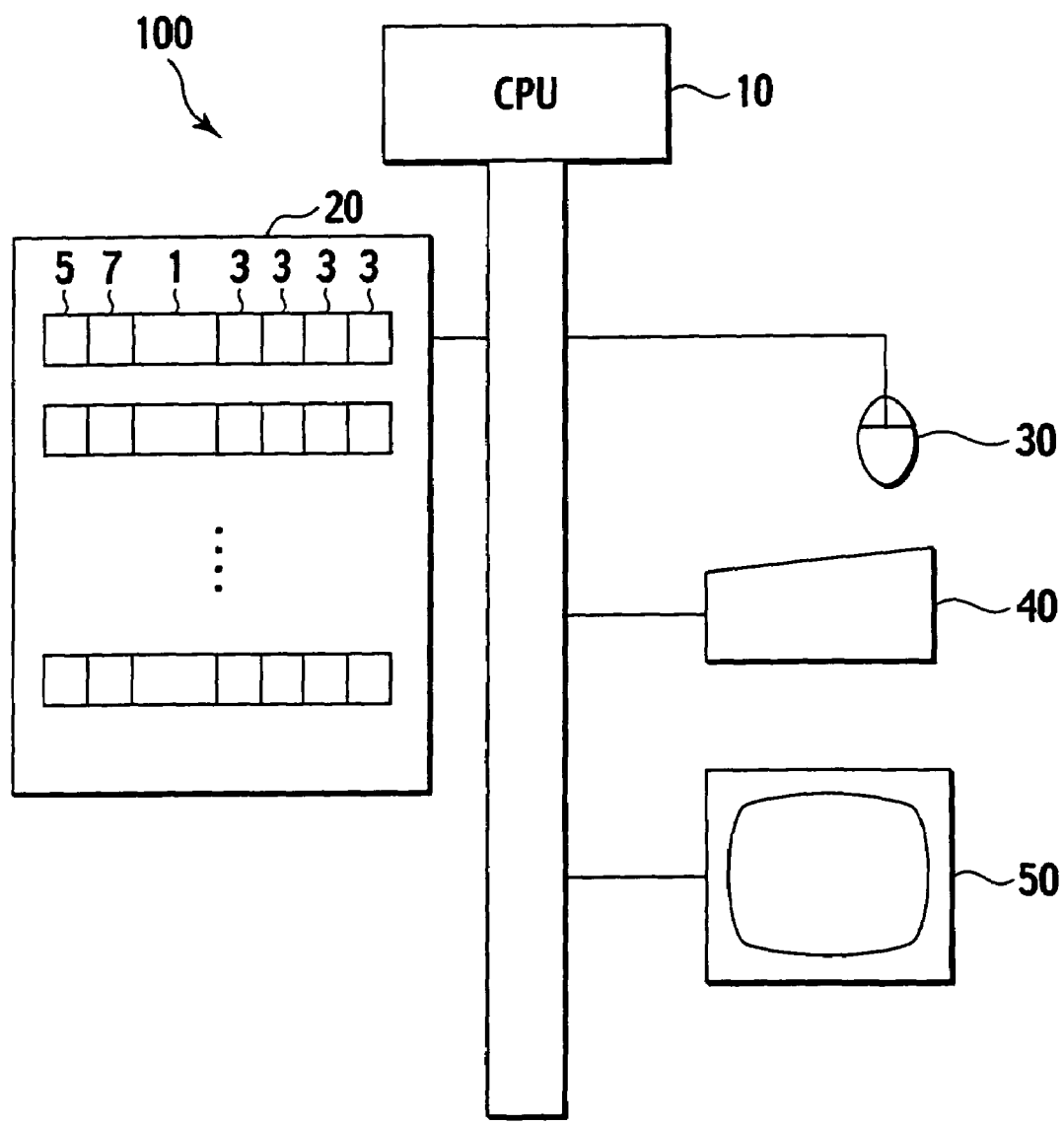
FIG. 4 is a diagram showing an embodiment of the case where the color presenting method of the invention is applied to a personal computer with a color presenting function.

FIG. 4 is a diagram showing an embodiment applying the color presenting method of the invention to a personal computer with the color presenting function.

A personal computer 100 with a color presenting function shown in FIG. 4 has a CPU 10, a storage 20 for storing a set of information of the color-blindness selection color 1 and the color 3 selected by person of normal color vision, a mouse 30, a keyboard 40, and a color display 50.

The storage 20 stores a set of the information of the color-blindness selection color 1 and the color 3 selected by person of normal color vision as shown in the conceptual diagram of FIG. 1. In FIG. 4, the inside of the storage 20 is also shown as a concept. Therefore, the inside of the storage 20 does not show storage areas. In practice, the information is stored as code information. For example, when the color value 7 is employed as it is as a code indicative of the color-blindness selection color 1, it is unnecessary to separately store the information of the color name 5 and the information of the color value 7.

When the operator operates the mouse 30 or keyboard 40 to display a selected color, the selected color is displayed on the color display 50.

Figure 5A:
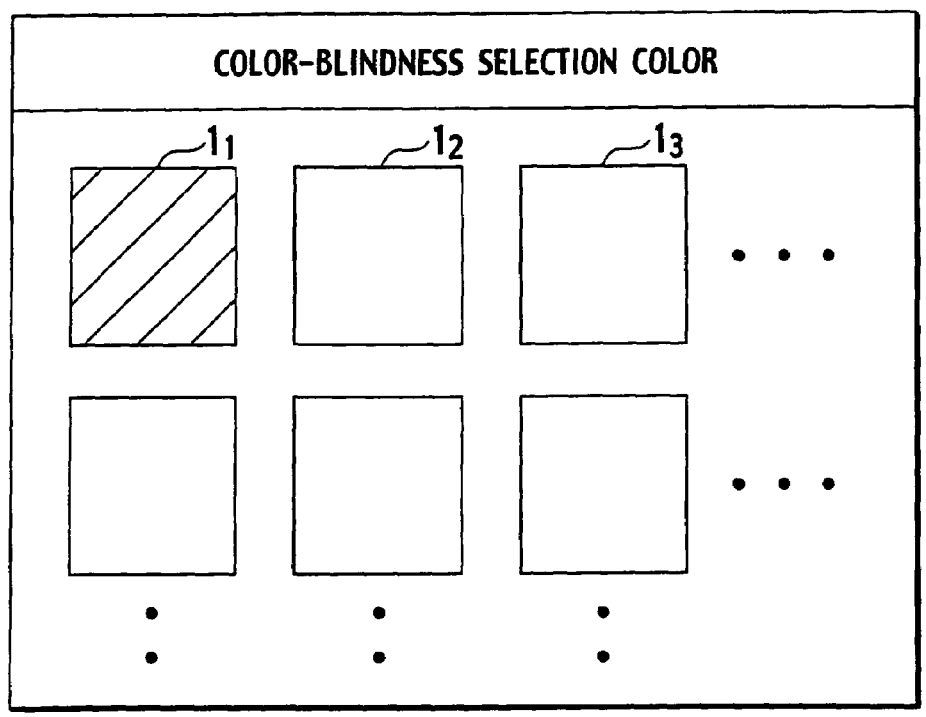
FIGS. 5A and 5B are diagrams showing an example of a display screen in a color display of the personal computer with the color presenting function.
Figure 5B:
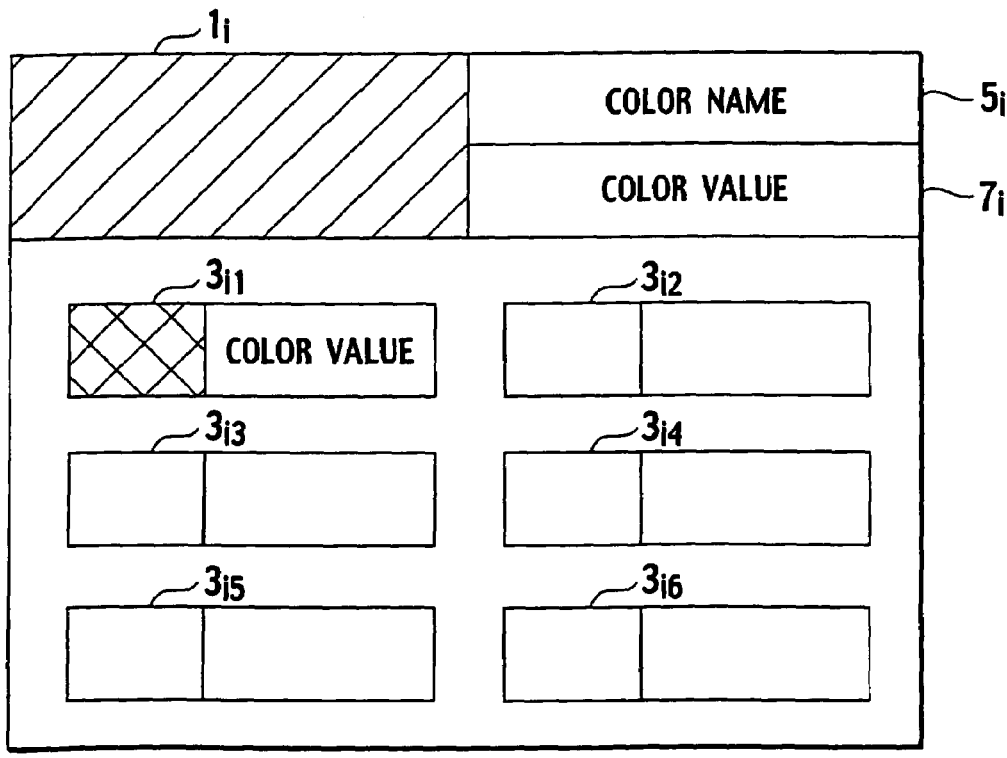

FIGS. 5A and 5B are diagrams showing an example of the display screen in the color display 50. A procedure executed when a color-blind person or a person of normal color vision operates the personal computer 100 with the color presenting function will be described hereinbelow.

First, a color-blind person or a person of normal color vision makes a window 60 displayed on the screen of the color display 50. The window 60 is a window for selecting a desired color-blindness selection color 1 from a plurality of color-blindness selection colors 1. In the window 60, color display frames corresponding to the number of color-blindness selection colors 1 are displayed, and an actual color-blindness selection color is painted in a corresponding color display frame. The color name 5 and the color value 7 may be also displayed together with each of the color-blindness selection colors 1.

The color-blind person or the person of normal color vision operates the mouse 30 or keyboard 40 to select a desired color from the displayed color-blindness selection colors 1. When a desired color is selected by a color-blind person or a person of normal color vision, a window 70 is displayed on the screen of the color display 50. Since the color-blind person does not perform an operation on the window 70, he/she returns to the window 60 and selects another color-blindness selection color 1 or finishes the operation.

On the other hand, the person of normal color vision can perform more-detailed color selection by an operation on the window 70. The window 70 is a window for selecting a desired color 3 selected by person of normal color vision from the plurality of colors 3 selected by person of normal color vision corresponding to the selected color-blindness selection color 1. In the window 70, the selected color-blindness selection color $1_i$ is displayed as a concrete color and the color name $5_i$ and the color value $7_i$ are also displayed. In the window 70, a plurality of colors $3_{i1}$ to $3_{i6}$ selected by person of normal color vision corresponding to the selected color-blindness selection color $1_i$ are also displayed. Further, corresponding color values $7_{i1}$ to $7_{i6}$ are also displayed for the colors $3_{i1}$ to $3_{i6}$ selected by person of normal color vision. In addition, corresponding color names $5_{i1}$ to $5_{i6}$ may be also displayed.

The person of normal color vision operates the mouse 30 or keyboard 40 to select a desired color from the displayed colors 3 selected by the person of normal color vision. In the case where the person of normal color vision wishes to select another color-blindness selection color, he/she returns to the window 60 and repeats similar processes. By the selecting process, as described above, the person of normal color vision can select a natural combination of colors oriented to color-blind persons. Under the condition of selecting only one color selected by person of normal color vision per color-blindness selection color, a combination of colors can be selected in consideration of color-blind persons.

A main object of the invention is to present only colors which can be distinguished from each other by a color-blind person. Consequently, on a medium on which colors are actually presented, they may not be reproduced accurately as colors in a color space of color-blind persons. To be specific, since there is a case that a color cannot be accurately reproduced depending on a color display, if colors are within the range color-blind persons can recognize, inaccuracy of colors actually expressed is allowed.

The color sample book (color chart) and the personal computer with the color presenting function have been described above as means realizing the color presenting method of the invention. The invention is not limited to them but other various modes can be also employed.

Although the names "color-blindness selection color" and "color selected by person of normal color vision" are employed above for convenience of logical explanation, there is no intention to discriminate against a color-blind person.

According to the invention as described above, a color-blind person can easily perform the work of designing a plurality of colors. When a person of normal color vision designs colors, colors which can be distinguished also by a color-blind person can be easily selected. Further, a plurality of colors which are seen as the same color by a color-blind person and are seen as different colors by a person of normal color vision can be also easily selected.

It should be understood that many modifications and adaptations of the invention will become apparent to those skilled in the art and it is intended to encompass such obvious modifications and changes in the scope of the claims appended hereto.

What is claimed is:

1. A color sample book wherein a plurality of colors which can be distinguished from each other by a color-blind person are painted, and for each of colors which can be distinguished by a color-blind person, a set of colors that can be distinguished by a person of normal color vision but are recognized as each said color by said color-blind person is painted.

2. A color presenting apparatus comprising:
a storage for storing information of a plurality of colors which can be distinguished from each other by a color-blind person, and storing, for information of each of colors which can be distinguished by said color-blind person, a set of information of a plurality of colors which can be distinguished from each other by a person of normal color vision but are recognized as said each color by said color-blind person;
a color display; and
a controller for displaying each of the colors which can be distinguished by said color-blind person and a plurality of colors which can be distinguished from each other by a person of normal color vision but are recognized as each said color by said color-blind person so as to be associated with each other on said color display on the basis of information stored in said storage.

* * * * *